United States Patent [19]

Kurz

[11] 4,348,178

[45] Sep. 7, 1982

[54] VIBRATIONAL ORTHODONTIC APPLIANCE

[76] Inventor: Craven H. Kurz, No. 6 North Star, Apt. 106, Marina del Rey, Calif. 90291

[21] Appl. No.: 929,329

[22] Filed: Jul. 31, 1978

Related U.S. Application Data

[63] Continuation of Ser. No. 756,268, Jan. 3, 1977, abandoned.

[51] Int. Cl.³ .............................................. A61C 3/00
[52] U.S. Cl. ........................................... 433/6; 433/5
[58] Field of Search ................. 32/14 B, 14 R, 14 C, 32/14 A, 58, DIG. 4; 128/62 A, 24 A, 172.1

[56] References Cited

U.S. PATENT DOCUMENTS

| | | | |
|---|---|---|---|
| 1,826,434 | 10/1931 | Reiss | 128/62 A |
| 2,531,222 | 11/1950 | Kesling | 32/14 B |
| 2,880,509 | 4/1959 | Strickler | 32/14 B |
| 2,912,976 | 11/1959 | Grund | 128/62 A |
| 3,115,139 | 12/1963 | Schneider | 128/62 A |
| 3,379,192 | 4/1968 | Warren, Jr. | 128/62 A |
| 3,385,291 | 5/1968 | Martin | 128/62 A |
| 3,481,329 | 12/1969 | Warren, Jr. | 32/58 |
| 4,011,616 | 3/1977 | Kennedy | 128/62 A |
| 4,123,844 | 11/1978 | Kurz | 32/14 D |

Primary Examiner—Gene Mancene
Assistant Examiner—John J. Wilson
Attorney, Agent, or Firm—Keith D. Beecher

[57] ABSTRACT

An orthodontic appliance is provided which consists of a tooth positioner mouth piece which contains impressions of the upper and lower teeth of a patient in corrected positions, and an electric motor mounted on the extra oral bow of a usual orthodontic headgear, and mechanically coupled to the mouth piece for introducing vibrations into the mouth piece. In a second embodiment, the mouth piece is pulsed by an electrically energized hydraulic pump.

4 Claims, 2 Drawing Figures

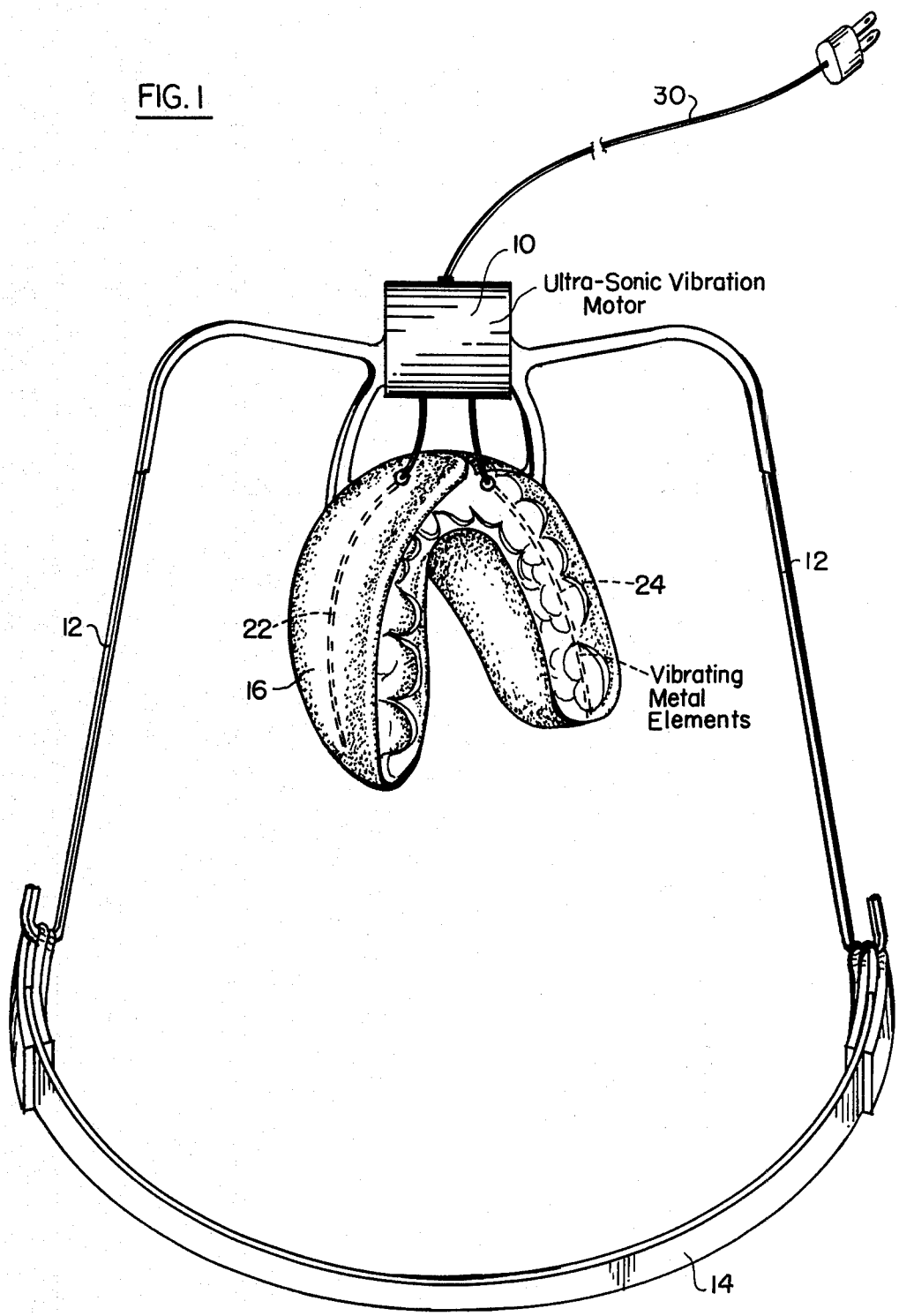

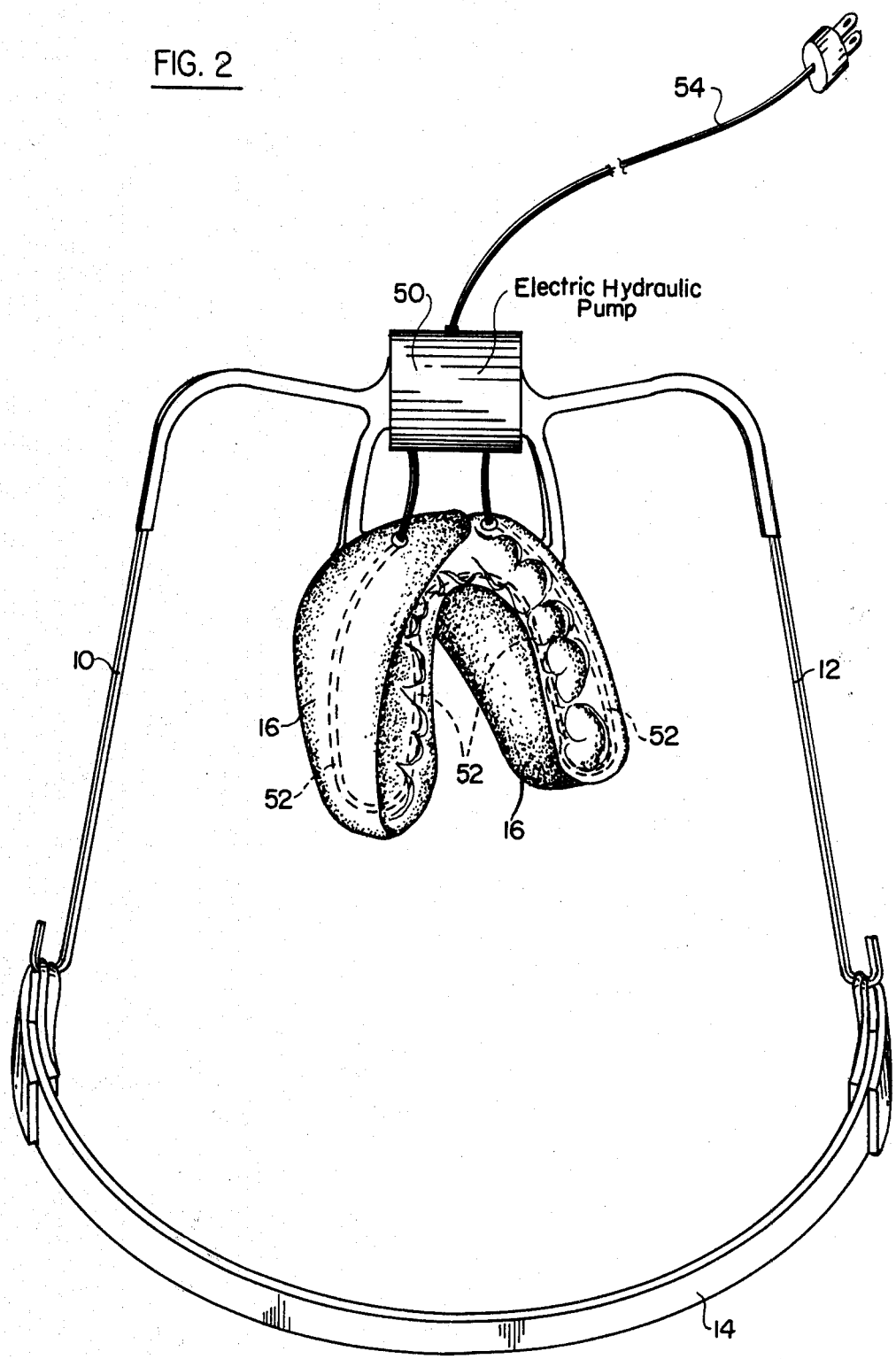

VIBRATIONAL ORTHODONTIC APPLIANCE

This application is a continuation of copending application Ser. No. 756,268 filed Jan. 3, 1977 now abandoned.

BACKGROUND OF THE INVENTION

Presently major teeth movement is performed by affixing orthodontic appliances in the form of brackets and tubes to the teeth. An arch wire interconnects the brackets and tubes. Teeth are moved along the arch wire by a variety of forces generated by appropriate resilient members.

When the teeth are near their ideal positions by the operation of the orthodontic appliances described in the preceding paragraph, it is the usual practice to form plaster models of the upper and lower arches. These plaster models are formed by first taking a negative impression of the teeth in an appropriate impression material, and then filling the negative impression with liquid plaster. After the plaster has set, the final result is a positive representation of the patient's teeth and adjacent tissue. The plaster models are then taken to a laboratory, and all the teeth are removed from the model separately with a very fine cutting saw. The teeth are then replaced on the base of the model in the ideal position and fixed in that position with a hard wax. Rubber under high pressure is then formed to fit the model.

The result of the foregoing is a mouth piece positioner with the impressions of all of the upper and lower teeth of the patient in their ideal positions. This prior art mouth piece positioner is then placed in the patient's mouth as a tooth positioner. The patient is instructed to bite continually into the positioner for a specified time and then to relax. The positioner must be worn for a certain number of hours, and there must be a continual biting down and relaxation of the teeth to move the teeth the small distance remaining to their ideal positions.

This continual clenching and relaxing of the teeth is laborious and tiring. However, the patient cooperation is mandatory in order to obtain the desired result, and many patients find the clenching too tiring to carry out on a prolonged basis. However, if the patient cooperates and continues to clench and force the teeth toward their ideal positions, very good results can be obtained using the prior art positioner.

The orthodontic appliance of the present invention makes use of such tooth positioner mouth pieces. However, the appliance of the invention has the advantage in that it achieves the desired results with minimal patient cooperation. The rubber positioner is activated by vibrational forces to press the teeth that are in malocclusion into a corrected position without continued clenching by the patient. The vibration of the rubber makes the positioner an active tooth moving appliance that exerts the correcting pressures of the positioner. Because of the reduced need for patient cooperation, the appliance of the invention can be used to treat a malocclusion through a series of positioners from the initial malocclusion to the finished correction without other orthodontic appliances. This results in reduced orthodontic material costs, reduced chair time, and increased patient's acceptance because the positioner is removable and can be taken out of the mouth on occasions when a person is in a public place.

BRIEF DESCRIPTION OF THE DRAWINGS

FIG. 1 is a representation of one embodiment of the invention, in which an ultra-sonic vibration motor introduces vibrations to a tooth positioner mouth piece; and FIG. 2 is a second embodiment in which an electric hydraulic pump introduces a pulsating motion to the positioner mouth piece.

DETAILED DESCRIPTION OF THE ILLUSTRATED EMBODIMENT

In the embodiment of FIG. 1, an electrically energized ultra-sonic vibration motor 10 is positioned in front of the mouth of the patient by an extra oral bow 12 of a conventional orthodontic headgear, which is held in place by a usual resilient neck strap 14.

A rubber tooth positioner mouth piece 16 is supported on the bow 12. Mouth piece 12 is preferably formed of rubber to provide maximum resiliency for rapid tooth movement and maximal patient comfort, the mouth piece is soft and resilient so that the patients can set their teeth comfortably in the positioner. Once the teeth are seated in the sockets in the positioner, the appliance immediately applies a gentle, tooth-moving force to the teeth to settle the teeth efficiently in their final positions. The visual side of the mouth piece contains impressions of the upper teeth of the patient in their ideal positions, and the hidden side of the mouth piece contains impressions of the lower teeth of the patient in their ideal positions. The mouth piece is formed in accordance with the usual prior art practice described briefly above.

A pair of elongated metal elements 22 and 24 extend through the mouth piece 16 from the motor 10, so that the ultra-sonic vibrations established by the motor may be transmitted to the mouth piece. The metal vibrational elements 22 and 24 are embedded between the upper and lower teeth impressions in the mouth piece 16. The vibrational elements are positioned in the mouth piece during the construction thereof. They are directly connected to the ultra-sonic vibration motor 10 which is mounted on the bow 12.

Although the motor 12 is shown equipped with an electric cord 30 which may plug into a usual alternating current receptacle, the motor could be self-contained, if so desired, with its own re-chargable or replaceable battery.

In the operation of the appliance of FIG. 1, the patient bites into the positioner mouth piece 16 which, as stated is mounted on the bow 12 which, in turn, is strapped around the patient's neck. The electric motor 10 is then energized. Appropriate clasps can be placed in the positioner mouth piece 16 to insure that it will remain firmly in the mouth even without a strong clenching pressure. This is important to insure continual positioning of the positioner during the sleeping hours.

The resulting vibrational appliance will gently place intermittent pressure on the teeth in the mouth piece positioner 16 which require movement. The teeth will be caused by the vibrating positioner to move in an efficient physiological manner, because the vibrating pressure of the positioner will break down tissue resistance in the adjacent bone to the movement of the teeth. The teeth will consequently move through the fibrous elements of the bone along the path of least resistance.

Moreover, the pressure on the teeth to be moved will be disseminated by the vibrational appliance of the invention to a large area throughout the adjacent bone by vibrational dissemination of forces, and consequently no pressure areas will be strong enough to result in reduced blood supply leading to the necrosis. It follows that optimal blood supply will lead to increased cellular activity. Specifically, there will be optimal oesteoclastic activity for bone resorption, and optimal oesteoblastic activity for bone apposition. The cellular elements of the tissue due to the continuation of good blood supply are in an optimal quantity to effect fast, efficient tooth movement without pain, root resorption or irreversible horizontal bone loss.

As explained briefly above, the tooth positioner mouth piece 16 is made of a resilient rubber so that when forces are placed on the teeth there is some give in the device. This helps prevent excessive pressurization of the boney tissue that could reduce blood supply to the area and cause the ineffecent reverse resorption. When the positioner is in the mouth of the patient, every time the patient swallows the teeth are pressed together lightly. This tends to force the misaligned teeth into their proper position.

By the use of the appliance of the present invention, malocculusions, no matter how pronounced can be corrected by a series of vibrating mouth piece positioners which vibrate the teeth in propressive stages towards their ideal occlusion without the problem of excessive patient cooperation. For example, any particular orthodontic problem cause can be analyzed, and a first vibrational positioner with a specified correction can be placed in the patient's mouth and held in place with the headgear, so that the teeth may be moved from their initial position to a point where the first positioner is no longer effective. A second vibrational positioner may then be inserted into the patient's mouth to move the teeth another increment toward the ideal occlusion, and so on. In this way, vibrational positioners may in a step-by-step manner carry the occlusion towards the ideal positions without the use of any other orthodontic appliances.

Therefore, by employing the vibrational techniques of the present invention, tooth positioner mouth pieces can be used fully to translate teeth from an initial malocclusion position to an ideal occlusion position. Because a tooth positioner mouth piece can easily move teeth between one and two millimeters, it is estimated that full treatment could be achieved in most cases with between four and five positioners. This provides orthodontic treatment without the need for fixed or removable appliances of the type which tend to collect food and cause increased tooth decalcification and carries, and this is achieved with minimal patient cooperation, and with minimal orthodontic chair time.

Histologically, the vibrational dissemination forces are light and directed over a large area. Thus, the blood supply in the pressurized areas is kept high resulting in increased cellular activity and fast, efficient tooth movement and stabilization. The vibrational movement is passed on to the root of the teeth, which helps to break down tissues fibrous resistance and facilitates the fast movement to teeth. Vibration iself helps increase the cellular activity by increasing blood circulation. Increased cellular activity and fluid exchange results in the optimal condition for tooth movement.

Because every tooth in the mouth is in the tooth positioner mouth piece, all the misaligned teeth are caused to move at once during the treatment which leads to a shorter treatment time. The rubber of the mouth piece has resiliency which protects against rigidly forcing teeth against boney walls and causing trauma to bone and root surface. No preparation of the natural tooth surface is required to effect tooth movement. Natural swallowing results in a light clench directing forces in a pulsational manner to the teeth which helps tooth movement. Long periods of wear can be prescribed without any resulting tooth damage, or fear of the teeth being moved too far in any direction. No root resorption or horizontal bone loss occurs in the use of the appliance of the invention, and tooth movement is virtually painless.

The embodiment of FIG. 2 includes many components of the embodiment of FIG. 1, and like elements are represented by the same numbers. In the embodiment of FIG. 2 the ultra-sonic vibration motor 10 of FIG. 1 is replaced by an electrically energized hydraulic pump 50. The hydraulic pump 50 is coupled to a length of rubber tubing 52 which extends through the mouth piece 16, in the same position as the vibrational elements 22 and 24 of FIG. 1. The hydraulic pump 50 is energized from a usual receptacle through an electric cord 54, or by a self-contained battery.

When the pump is activiated, it forces a hydraulic fluid through the tubular member 52 creating a pulsating action in the mouth piece 16. The same principles of movement apply in the second embodiment as in the first embodiment. The set positions of the teeth in the positioner of the second embodiment are activated by a pulsing action. The effect is to disseminate the orthodontic pressure to the teeth and adjacent tissue. The pulsation of the appliance reduces the necessity for the patient to clench in order to receive benefit from the appliance.

The pulsations that occur in the positioner mouth piece 16 are generated by the expansion and contaction of the rubber tubing 52 which is embedded in the rubber of the positioner mouth piece during its fabrication. The electrically energized hydraulic pump 50 is mounted on the bow 12 of the external headgear, as shown.

When the pump 50 is activated, hydraulic fluid is forced into the rubber tubing 52, as described above, causing cyclic expansion and contaction of the tubing in the positioner 16. This cyclic expansion and contraction is passed onto the positioner causing it to function as a dynamic appliance that rythmically applies pressure to the teeth. All the advantages of light pulsation pressure described previously herein apply equally to the appliance of the second embodiment.

While particular embodiments of the invention have been shown and described, modifications may be made. It is intended in the claims to cover the modifications which come within the spirit and scope of the invention.

What is claimed is:

1. An active tooth-moving orthodontic appliance for moving teeth that are in maloclusion into corrected positions without clenching, comprising: a resilient tooth positioner mouthpiece containing impressions of the teeth of a patient in corrected position; and means coupled to the mouthpiece for imparting tooth-moving vibrational forces to the mouthpiece to press the teeth that are in maloclusion into the corrected positions, in which said means comprises an ultra-sonic electric motor for introducing vibratory motion to the mouthpiece.

2. The orthodontic appliance defined in claim 1; in which said means further comprises elongated metallic elements extending from the motor through the mouth piece.

3. The orthodontic appliance defined in claim 2, and which includes an extra oral bow for supporting said means.

4. An active tooth-moving orthodontic appliance for moving teeth that are in maloclusion into corrected positions without clenching, comprising: a resilient tooth positioner mouthpiece containing impressions of the teeth of a patient in corrected position; and means coupled to the mouthpiece for imparting tooth-moving vibrational forces to the mouthpiece to press the teeth that are in maloclusion into the corrected positions, in which said means comprises an electrically energized hydraulic pump, and rubber tubing extending from said pump through said mouthpiece.

* * * * *